United States Patent
Kojima et al.

(10) Patent No.: US 11,454,756 B2
(45) Date of Patent: Sep. 27, 2022

(54) PLASTIC OPTICAL FIBER FOR MEDICAL DEVICE LIGHTING AND MEDICAL DEVICE LIGHTING USING SAME

(71) Applicant: Toray Industries, Inc., Tokyo (JP)

(72) Inventors: Hideki Kojima, Nagoya (JP); Hironobu Maeda, Nagoya (JP); Shinji Sato, Nagoya (JP); Hidekazu Kunieda, Tokyo (JP); Satoshi Matsuba, Nagoya (JP)

(73) Assignee: Toray Industries, Inc., Tokyo (JP)

( * ) Notice: Subject to any disclaimer, the term of this patent is extended or adjusted under 35 U.S.C. 154(b) by 406 days.

(21) Appl. No.: 16/646,724

(22) PCT Filed: Sep. 18, 2018

(86) PCT No.: PCT/JP2018/034392
§ 371 (c)(1),
(2) Date: Mar. 12, 2020

(87) PCT Pub. No.: WO2019/053160
PCT Pub. Date: Mar. 28, 2019

(65) Prior Publication Data
US 2020/0301064 A1    Sep. 24, 2020

(30) Foreign Application Priority Data
Sep. 22, 2017   (JP) .............................. JP2017-182045

(51) Int. Cl.
*G02B 6/02* (2006.01)
*A61B 1/00* (2006.01)
(Continued)

(52) U.S. Cl.
CPC ........ *G02B 6/02038* (2013.01); *A61B 1/0017* (2013.01); *A61B 1/00167* (2013.01);
(Continued)

(58) Field of Classification Search
None
See application file for complete search history.

(56) References Cited

U.S. PATENT DOCUMENTS

| | | | | |
|---|---|---|---|---|
| 4,398,790 A * | 8/1983 | Righini | ................. | B23K 26/06 606/17 |
| 4,872,740 A * | 10/1989 | Terada | ............... | A61B 1/00165 385/117 |
| 2002/0161282 A1 | 10/2002 | Fulghum | | |
| 2012/0020637 A1* | 1/2012 | Maeda | ................. | C08F 214/26 385/145 |

FOREIGN PATENT DOCUMENTS

| | | |
|---|---|---|
| JP | 8-43678 A | 2/1996 |
| JP | 08194171 A * | 7/1996 |

(Continued)

OTHER PUBLICATIONS

Katsunari Okamoto, "Optical Communication Techniques (4), Light propagation in optical fibers," The Journal of the Institute of Television Engineers of Japan, vol. 41, No. 9, 1987, pp. 836-844.
Toray Industries, Inc., Raytela Polymer Optical Fiber.

*Primary Examiner* — Michelle R Connelly
(74) *Attorney, Agent, or Firm* — DLA Piper LLP (US)

(57) ABSTRACT

A plastic optical fiber for a medical device lighting decreases the cost of a lens and simplify the design of a lighting apparatus, wherein the plastic optical fiber for a medical device includes a core composed of a (co)polymer containing methyl methacrylate as a main component and is characterized by including a cladding material composed of a copolymer having a fluorine weight composition ratio of 60 to 74%, and by having a theoretical numerical aperture, NA, of 0.48 to 0.65 and, thus, the plastic optical fiber has a high numerical aperture and also has excellent translucency and flexibility.

14 Claims, 2 Drawing Sheets

(51) Int. Cl.
    *A61B 1/06*           (2006.01)
    *A61B 1/07*           (2006.01)
    *G02B 6/06*           (2006.01)
    *G02B 23/24*         (2006.01)
    *G02B 1/04*           (2006.01)
    *A61B 5/00*           (2006.01)
    *G02B 6/12*           (2006.01)

(52) U.S. Cl.
    CPC .............. *A61B 1/0661* (2013.01); *A61B 1/07* (2013.01); *A61B 5/42* (2013.01); *G02B 1/046* (2013.01); *G02B 1/048* (2013.01); *G02B 6/02033* (2013.01); *G02B 6/06* (2013.01); *G02B 23/2469* (2013.01); *G02B 2006/12035* (2013.01)

(56) References Cited

FOREIGN PATENT DOCUMENTS

| | | | | |
|---|---|---|---|---|
| JP | 10-274716 | A | | 10/1998 |
| JP | 2857411 | B2 | | 2/1999 |
| JP | 11-95044 | A | | 4/1999 |
| JP | 2002-98864 | A | | 4/2002 |
| JP | 2002148451 | A | * | 5/2002 |
| JP | 2002-535025 | A | | 10/2002 |
| JP | 4310899 | B2 | | 8/2009 |
| JP | 2011-209487 | A | | 10/2011 |
| KR | 20120005434 | A | * | 1/2012 ......... G02B 6/02033 |
| WO | 2015/015996 | A1 | | 2/2015 |

* cited by examiner

PLASTIC OPTICAL FIBER FOR MEDICAL DEVICE LIGHTING AND MEDICAL DEVICE LIGHTING USING SAME

TECHNICAL FIELD

This disclosure relates to plastic optical fibers for medical device lightings and medical device lightings produced using the same.

BACKGROUND

An example of a lighting to be used for a medical device is a combination of a light source and a light guide that transmits light from the light source to the end of the light guide and radiates the light to an irradiated object. One such light guide is produced using a single optical fiber or a plurality of optical fibers bundled to increase the optical transmission quantity.

In recent years, image pickup devices typified by CCDs have been made smaller, thus enabling an observation probe of an endoscope to have a smaller diameter. Accordingly, a light guide incorporated in the probe is also desired to have a smaller diameter, and an optical fiber having a smaller diameter and still affording a large quantity of optical transmission is desired. In addition, allowing an observation probe of an endoscope to have a smaller diameter makes it possible to directly observe the inside of a narrow tube, for example, the bile duct or the pancreatic duct, which the probe has been unable to enter hitherto. The bile duct and the pancreatic duct are very thin lumens, 5 mm to 10 mm, and an endoscope to be inserted in these lumens is limited to having an outer diameter of 3 mm to 4 mm. In addition, an observation probe of an endoscope to be inserted in the bile duct or the pancreatic duct is usually passed through the opening in the side of the observation probe of a side view type of duodenum endoscope, inserted into the duodenal papilla, and then inserted into the bile duct or the pancreatic duct. The former probe is guided in the direction at 90° to the side opening of the duodenum endoscope and, thus, a desirable optical fiber is one which does not decrease the light quantity when bent.

Optical fibers are roughly classified into glass optical fibers and plastic optical fibers (hereinafter referred to as POF for short). Light sources suitably used for medical devices are halogen light sources, the heating value of which is easily increased and, thus, glass optical fibers, which have high heat resistance, are used.

However, POFs have an optical transmission portion having a larger core diameter and have a larger numerical aperture than glass optical fibers, even if having the same optical fiber diameter as glass optical fibers. Accordingly, POFs can obtain a larger optical transmission quantity, and also make it possible to diminish a decrease caused in light quantity when bent, because the permissible angle of reflection in the optical fiber increases as the numerical aperture increases. In addition, POFs are characterized in that they are less easily broken when bent. As above-mentioned, a plastic optical fiber having a larger numerical aperture is desired as a plastic optical fiber for a medical device lighting.

In this regard, a theoretical numerical aperture is determined from a difference in refractive index between a core and a cladding, using the following Equation:

$$\text{Numerical Aperture} = ((\text{Refractive Index of Core})^2 - (\text{Refractive Index of Cladding})^2)^{1/2}.$$

A POF is usually a double-layer including a core and a cladding and, for the core, a polymer having excellent translucency is generally used, a typical example of which is polymethyl methacrylate (hereinafter referred to as PMMA for short). On the other hand, for the cladding, a fluorine-containing polymer is widely used because the cladding needs to have a lower refractive index than refractive index of the core to trap light within the core.

The following three types of fluorine-containing polymers are commonly used for a cladding, and any of the polymers has a numerical aperture of approximately 0.47 or approximately 0.50:

(1) vinylidene fluoride copolymers such as a vinylidene fluoride/tetrafluoroethylene copolymer and a vinylidene fluoride/hexafluoroacetone copolymer
(2) POFs in which a copolymer of fluoroalkyl methacrylate and methyl methacrylate is used for cladding
(3) POFs in which a copolymer of long chain fluoroalkyl methacrylate and methyl methacrylate is used for cladding.

A numerical aperture such as above produces a sufficient effect for the sake of lighting compared to an effect produced by a glass optical fiber. A larger numerical aperture results in enlarging the lighting range, thus enhancing visibility further during surgery and, accordingly, is preferable. To allow a POF to have a higher numerical aperture, it is necessary to copolymerize a monomer having a higher fluorine content and having an even lower refractive index. One of such POFs is a proposed POF the cladding of which is a polymer (the tradename "THV200" from Dyneon) in which hexafluoropropylene as a third component is copolymerized with vinylidene fluoride and tetrafluoroethylene (see, for example, JP 2857411 B2). This has a high numerical aperture of 0.60, but has a problem, for example, in that the cladding material is too flexible to wind and tacky when the POF is wound up. Thus, the POF is difficult to commercialize.

To improve this, another proposed POF has a double-layer cladding structure in which "THV200" is used as a cladding material, which is further covered and protected by a protective layer containing a vinylidene fluoride copolymer described in the above-mentioned JP '411, a vinylidene fluoride homopolymer, nylon 12, or the like (see, for example, JP H11-95044 A and JP H10-274716 A). However, such a double-layer cladding structure requires a special spinneret and thus leads to low production capacity and high cost, compared with a monolayer cladding structure. Such a double-layer cladding structure also involves dividing the thin layer cladding into two, resulting in low adhesion and low mechanical characteristics, and thus poses a problem of flexibility.

On the other hand, Dyneon has products which are terpolymer compositions having the same copolymer components but at varied composition ratios, examples of the products including "THV400" and "THV500," which have a smaller vinylidene fluoride composition. However, those polymers have low translucency and are not suited for optical fiber applications, although the polymers do not have a tackiness problem such as caused by "THV200."

A proposed POF having a high numerical aperture is a POF the cladding of which is a polymer in which a perfluoroalkylvinylether as a fourth component is copolymerized with vinylidene fluoride, tetrafluoroethylene, and hexafluoropropylene (see, for example, JP 4310899 B2).

When glass optical fiber is used for a medical device lighting, light outgoing from the end face of the light guide is similar to parallel light, and thus, a structure is proposed, in which light is diffused through a lens for lighting, using a concave face as the light guide end face side of the lens (see, for example, WO 2015/015996).

However, such a medical device lighting produced using a glass optical fiber as described in WO '996 involves using a concave lens as a lens for lighting, and thus necessitates making the lens thick, accordingly posing a problem in that light transmittance is decreased, and that it is more difficult to design such a device.

It could therefore be helpful to provide a plastic optical fiber for a medical device lighting, the plastic optical fiber having a high numerical aperture and further having excellent translucency and flexibility and to thereby decrease the cost of a lens and simplify the design of a lighting apparatus.

SUMMARY

We discovered that a POF achieves a large quantity of light transmission when used in the form of a single fiber, does not break or decrease in light quantity when bent, and thus is most suitable as a plastic optical fiber for a medical device lighting, wherein the POF includes a core composed of a (co)polymer containing methyl methacrylate as a main component and a cladding composed of a fluorine-containing (co)polymer having a fluorine weight composition ratio of 60 to 74%, and wherein the POF has a theoretical numerical aperture, NA, of 0.48 to 0.65.

We thus provide a plastic optical fiber for a medical device, including a core composed of a (co)polymer containing methyl methacrylate as a main component, wherein the plastic optical fiber for a medical device lighting is characterized by including a cladding composed of a copolymer having a fluorine weight composition ratio of 60 to 74%, and by having a theoretical numerical aperture, NA, of 0.48 to 0.65.

We make it possible to provide a POF that is suitably used for a medical device lighting, particularly for an endoscope to be inserted into the bile duct and the pancreatic duct, and that has a high numerical aperture and further has excellent translucency and flexibility. We also make it possible to decrease the cost of a lens and simplify the design of a lighting apparatus.

REFERENCE SIGNS LIST

Figure 1:
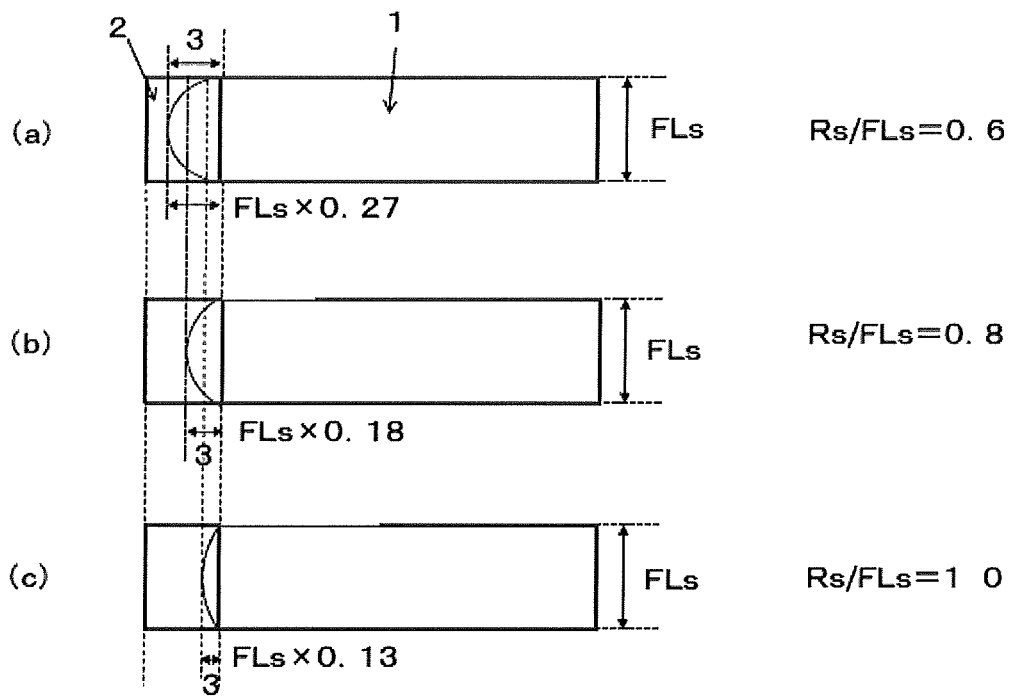
FIGS. 1(*a*)-(*c*) show schematic views that each depict the lens concave thickness of a lens for lighting.

1: Light Guide
2: Lens for Lighting
3: Lens Concave Thickness
4: Lens Width

DETAILED DESCRIPTION

In our plastic optical fiber for a medical device lighting (a POF for a medical device lighting), a (co)polymer forming a core and containing methyl methacrylate as a main component is: a copolymer mainly containing PMMA or methyl methacrylate (a copolymer obtained by copolymerizing, for example, (meth)acrylic acid ester, (meth)acrylic acid, substituted styrene, N-substituted maleimide, or the like); a modified polymer obtained by polymeric reaction thereof such as glutaric anhydride or glutaralimide; or the like. In this regard, examples of (meth)acrylic acid esters include methyl acrylate, ethyl methacrylate, butyl methacrylate, t-butyl methacrylate, cyclohexyl methacrylate, benzyl methacrylate, phenyl methacrylate, bornyl methacrylate, adamantyl methacrylate and the like. Examples of substituted styrenes include styrene, methyl styrene, α-methyl styrene and the like. Examples of N-substituted maleimides include N-isopropylmaleimide, N-cyclohexylmaleimide, N-methylmaleimide, N-ethylmaleimide, N-o-methylphenylmaleimide and the like. A plurality of these copolymerization components may be used, and components other than these may be used in small amounts. In addition, the copolymer may contain a stabilizer such as antioxidant in an amount enough not to adversely affect the translucency. Among these polymers, one which is substantially a PMMA is most preferable from the viewpoint of productivity, translucency, environment resistance and the like.

The theoretical numerical aperture, NA, is 0.48 to 0.65. The theoretical numerical aperture of less than 0.48 makes it necessary to increase the curvature of a lens for lighting to maintain the lighting range, and thus, does not enable the lens width to be smaller. Such a thicker lens causes a problem in that the light quantity attenuates accordingly. In addition, such a lens causes the plastic optical fiber to undergo a larger bending loss, and decreases the light quantity. When the theoretical numerical aperture is more than 0.65, the production of a fluoropolymer used as a cladding material to achieve such a high numerical aperture is itself difficult.

The fluorine weight composition ratio of the cladding is 60 to 74%. The fluorine weight composition ratio of less than 60% causes an acrylate-based or methacrylate-based monomer having a low fluorine content to be used for the polymer composition for the cladding, which thus results in having lower flexibility. The fluorine content of more than 74% causes difficulty of the production itself of a fluoropolymer.

The cladding preferably has a bending elastic modulus of 20 to 200 MPa. In general, a plastic optical fiber used in medical applications goes into very small parts of a human body, driving the end of the fiber precisely, and thus, preferably has durability to repeated bending. Allowing the bending elastic modulus of the innermost layer cladding to be 20 to 200 MPa enables this characteristic to be satisfied.

For a plastic optical fiber for a medical device lighting, it is preferable that the cladding is composed of a copolymer containing
  10 to 30 wt % of hexafluoropropylene,
  45 to 75 wt % of tetrafluoroethylene,
  10 to 35 wt % of vinylidene fluoride, and
  1 to 10 wt % of perfluoroalkylvinylether; and
the fluorine weight composition ratio of the cladding is 70 to 74%. The composition within this range makes it easier to achieve a lower refractive index and less crystallization (clear and colorless). In addition, such a composition effects excellent adhesion to the core of the (co)polymer mainly containing methyl methacrylate. In addition, such a composition affords excellent mechanical characteristic such as flexibility and also excellent tackiness and heat resistance. As a result, the theoretical numerical aperture, NA, is preferably 0.60 to 0.65 to maintain a high numerical aperture and achieve well-balanced POF characteristics.

Furthermore, the cladding is preferably a copolymer composed of
- 14 to 25 wt % of hexafluoropropylene,
- 49 to 70 wt % of tetrafluoroethylene,
- 14 to 30 wt % of vinylidene fluoride, and
- 2 to 7 wt % of perfluoroalkylvinylether; and it is preferable that the fluorine weight composition ratio of the cladding is 71 to 74%, and the plastic optical fiber preferably has a theoretical numerical aperture, NA, of 0.61 to 0.65.

To maintain a high numerical aperture, perfluoroalkylvinylethers can be used as other copolymerizable components.

The copolymers forming the cladding preferably have properties including a Shore D hardness (ASTM D2240) of 35 to 55 and a melt flow index (265° C./5 kg) of 5 to 80 g/10 minutes.

In addition, the cladding preferably has a thickness of 2 to 20 more preferably 3 to 16 still more preferably 4 to 12 μm, yet more preferably 4 to 10

The plastic optical fiber further has one or more cladding layers outside of the above-mentioned cladding, wherein the outermost cladding layer is preferably composed of a copolymer containing
- 10 to 35 wt % of ethylene,
- 45 to 69 wt % of tetrafluoroethylene,
- 20 to 45 wt % of hexafluoropropylene, and
- 0.01 to 10 wt % of a fluorovinyl compound represented by Equation (1)

$$CH_2=CX^1(CF_2)_nX^2 \tag{1}$$

wherein $X^1$ represents a fluorine atom or hydrogen atom; $X^2$ represents a fluorine atom, hydrogen atom, or carbon atom; and n is an integer of 1 to 10.

In this regard, the one or more cladding layers may structurally be further covered by a protective layer, 2 to 100 μm, which is: a vinylidene fluoride (co)polymer such as a vinylidene fluoride/tetrafluoroethylene copolymer, a vinylidene fluoride/hexafluoroacetone copolymer, or a vinylidene fluoride homopolymer; an ethylene/tetrafluoroethylene/hexafluoropropylene (co)polymer; the same (co)polymer mainly containing methyl methacrylate as the one included in the core; or a polymer such as nylon 12. This protective layer may contain, for example, a pigment such as carbon black to be colored.

Our POF for a medical device lighting can be produced in the same manner as a common production method. For example, a conjugate spinning method is preferably used, wherein a core material and a cladding material in a heated melting state are discharged through a composite spinneret for concentric circular conjugation to form a core-cladding double-layer structure having a core and a cladding. Subsequently, the structure is generally allowed to undergo an approximately 1.2- to 3-fold stretching processing for the purpose of enhancing the mechanical characteristics, and is thus formed into a POF. For the purpose of enhancing the transparency of the core material, a continuous conjugate melt prevention method is more preferably used, wherein a series of steps including purification of a monomer, polymerization, conjugate melt with a cladding material, and stretching processing is carried out in a hermetically sealed system. If a protective layer is added, the protective layer can be produced by a known method, and a conjugate spinning method carried out simultaneously for three layers is preferably used.

The outer diameter of this POF is usually approximately 0.1 to 3.0 mm, may be determined suitably in accordance with the purpose, and is preferably 0.1 to 2.0 mm, more preferably 0.1 to 1.5 mm, from the viewpoint of receivability into an observation probe of an endoscope and handleability. Furthermore, in an observation probe of an endoscope that can be inserted into the bile duct or the pancreatic duct, the diameter of the observation probe is preferably 7 mm or less, more preferably 4 mm or less, considering the necessity to receive a POF together with an image pickup device and forceps for medical use and the necessity to bend the observation probe at 90 degrees in inserting the observation probe into the bile duct or the pancreatic duct. In addition, the outer diameter of the POF is more preferably 0.1 to 1.0 mm.

Our POF for a medical device lighting can further be coated with a resin and formed into a cord, examples of such resins including polyethylene, polypropylene or copolymers thereof, blend products, olefinic polymers containing an organic silane group, ethylene-vinyl acetate, polyvinyl chloride, polyvinylidene fluoride, polyamide resins such as nylon 12, polyester resins, nylon elastomers, polyester elastomers, urethane resins, and fluorine resins. The coating layer may be a monolayer or a multilayer, and the multilayer may include a tension member such as Kevlar™ between the layers. These coating materials may contain a stabilizer such as an antioxidant, age-registor, or UV stabilizer, besides a flame retardant. In this regard, the coating layer can be formed by a known method such as a melt-extrusion molding method carried out using a cross head die.

An example of a lighting to be used for a medical device is a combination of a light source and a light guide that transmits light from the light source to the end of the light guide and radiates the light to an irradiated object. The light guide includes our POF. The light guide may include one POF, or may include a bundle of two or more POFs. The light guide enables lighting light radiated from the light source to be guided to the end. The end preferably has a lens for lighting disposed thereon. The light guided by the light guide is radiated through the lens for lighting into a specimen, wherein the lens for lighting is disposed on the end of the inserted portion. A lighting optical system may be formed of one light guide or a combination of two or more light guides. If necessary, the diameter of the observation probe is made small preferably by inserting 10 or less POFs in the light guide.

Examples of usable light sources include existing light sources such as: halogen lamps that are brighter than common incandescent bulbs; xenon lamps that have high luminance and are closer to natural light; and LEDs that are light sources having high luminance. LED light sources are preferable in that they have high luminance and generate less heat when turned on.

It is preferable that the medical device lighting includes a light source and a light guide which transmits light from the light source to an end of the light guide and radiates the light to an irradiated object, a lens for lighting being disposed on the end face of the end of the light guide, wherein the major axis diameter, $FL_L$, of the end face and the minor axis diameter, $FL_S$, of the end face have a relationship of $0.9 \leq FL_S/FL_L \leq 1$. Allowing $FL_S/FL_L$ to be 0.9 or more makes it easier to carry out a step of adjusting the positions of the end face of the plastic optical fiber and the lens and to design the incorporation of a fiber in the light guide.

It is preferable that the medical device lighting includes a light source and a light guide that transmits light from the light source to an end of the light guide and radiates the light to an irradiated object, a lens for lighting being disposed on the end face of the end of the light guide, wherein the light guide side of the lens for lighting has a concave surface, and the curvature radius, $R_S$, of the minor axis of the lens and the minor axis diameter, $FL_S$, of the end face of the light guide have a relationship of $R_S/FL_S>0.7$. Allowing $R_S/FL_S$ to be >0.7 makes it possible that the minimum thickness of the lens for lighting is smaller relative to the minor axis diameter of the end face of the lens side of the light guide to make the lens thinner. This makes it possible to decrease the cost of a lens and simplify the design of a lighting apparatus. More preferably, $R_S/FL_S$ is ≥0.9.

The lens for lighting may be a spherical lens or an aspherical lens. In an aspherical lens, the curvature radius is determined with the lens regarded as having a spherical shape. The shape of a lens is measured using a laser interferometer. In a spherical lens, the curvature can be determined in a single uniform way. In an aspherical lens, the curvature can be determined using a theoretical formula for asphericity.

In addition, the lens concave thickness of the lens for lighting is preferably 0.25 times or less compared to the minor axis diameter of the light guide. The thickness is more preferably 0.16 times or less compared to the minor axis diameter of the light guide.

FIG. 1 shows schematic views that each depict the lens concave thickness of a lens for lighting. A lens for lighting 2 in plano-concave shape is disposed on the end of a light guide 1. A lens concave thickness 3 is a thickness corresponding to the depth of the concave portion of the concave surface side of the lens for lighting. In FIG. 1 (a), $R_S/FL_S=0.6$ applies under the conditions where the minor axis width of the lens for lighting 2 is made identical to the minor axis width of the light guide 1. The lens concave thickness 3 is larger. In (b) and (c) in FIG. 1, the values of $R_S/FL_S$ are 0.8 and 1.0 respectively under the same conditions as in (a). The larger the value is, the smaller the lens concave thickness 3 is. When the minor axis width of the lens for lighting 2 is made identical to the minor axis width of the light guide 1 as in (a) to (c) in FIG. 1, the values of the lens concave thicknesses 3 in (a) to (c) in FIG. 1 are $FL_s \times 0.27$, $FL_s \times 0.18$, and $FL_s \times 0.13$ respectively.

Figure 2:
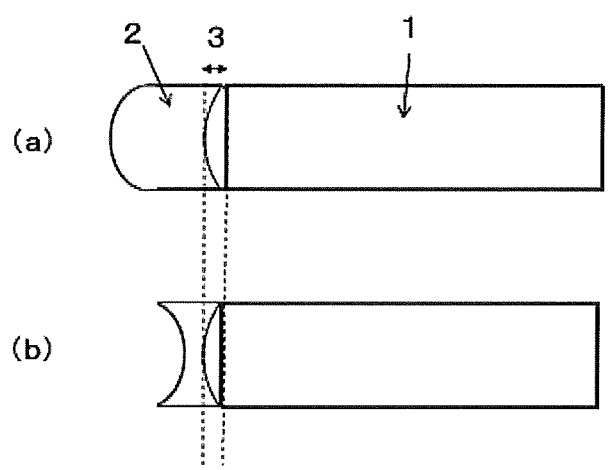
FIGS. 2(*a*) and (*b*) show schematic views that each depict the lens concave thickness of a lens for lighting.

FIG. 2 shows schematic views which each depict the lens concave thickness of a lens for lighting, wherein the different lenses for lighting have different shapes. In (a) to (b) in FIG. 2, the lenses for lighting have a concave-convex shape and a concave-concave shape respectively. In these examples, the lens concave thickness is a thickness corresponding to the depth of a concave portion of the lens, wherein the concave portion is disposed on the end face of the light guide.

When the lens for lighting is a plane lens having no concave or convex portion, the thickness of the lens is the thickness of the whole lens.

Furthermore, it is preferable that the width of the lens for lighting is approximately equal to the minor axis diameter of the light guide. More specifically, the width is preferably 0.9 times or more and 1.5 times or less compared to the minor axis diameter of the light guide. The width in this range makes it possible that light outgoing from the outermost edge of the end face of the light guide can be caught within the lens without making the lens larger than necessary. The width is more preferably 0.95 times or more and 1.3 times or less compared to the minor axis diameter of the light guide. As used herein, the lens width refers to the minor axis diameter of the lens. That is, the width is the width of the lens in the minor axis direction, wherein the lens is disposed such that this minor axis direction is along the minor axis of the light guide.

Figure 3:
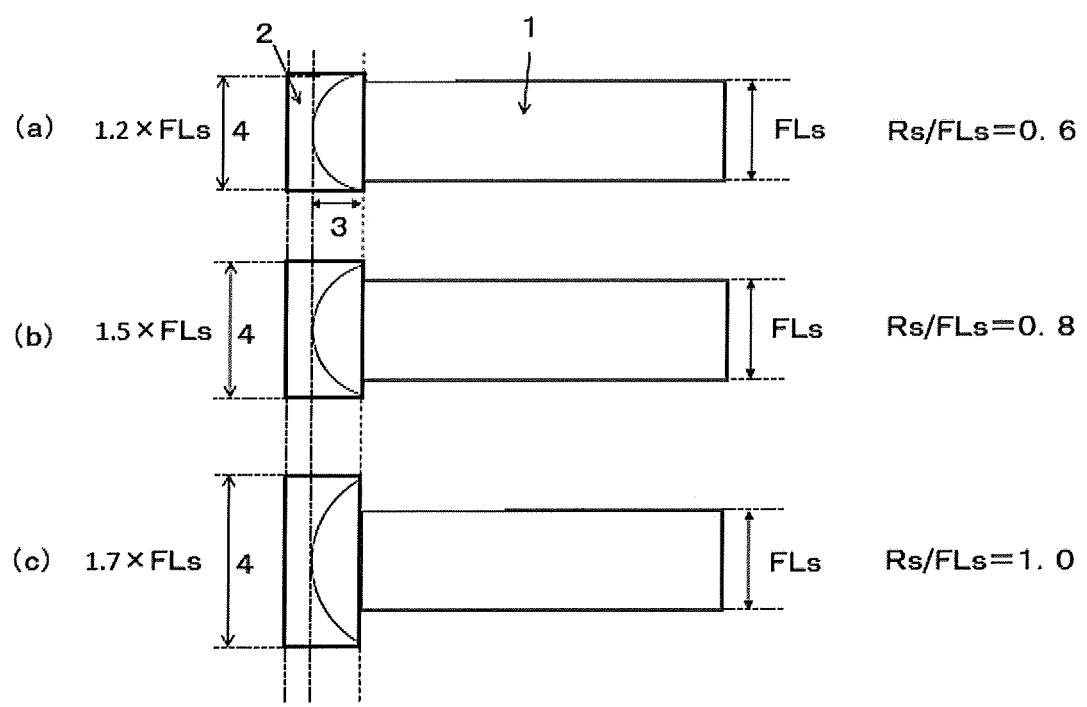
FIGS. 3(*a*)-(*c*) show schematic views that each depict the lens width of a lens for lighting.

FIG. 3 shows schematic views which each depict the lens width of a lens for lighting. A lens for lighting 2 in plano-concave shape is disposed on the end of a light guide 1. In FIG. 3 (a), $R_S/FL_S=0.6$ applies under the conditions where the lens concave thickness 3 of the lens for lighting 2 is made identical to half the length of the minor axis width of the light guide 1. The lens width 4 is smaller. In (b) and (c) in FIG. 3, the values of $R_S/FL_S$ are 0.8 and 1.0 respectively under the same conditions as in (a). The larger the value is, the larger the lens width 4 is. When the lens concave thickness 3 of the lens for lighting 2 is a given value, $FL_s \times 0.27$, as in (a) to (c) in FIG. 3, the values of the lens widths 4 in (a) to (c) in FIG. 3 are $FL_s \times 1.2$, $FL_s \times 1.5$, and $FL_s \times 1.7$ respectively.

The material of the lens for lighting may be glass or plastic. Examples of glass materials to be used for optical systems include, but are not limited to, optical glasses, substrate glasses, and glass lenses; examples of optical glasses include BK7 and synthetic quarts; examples of substrate glasses include "Pyrex" (registered trademark) used as a material of sheet glass, and glasses called white sheet glass and blue sheet glass; and examples of glass lenses include crown glass and flint glass. In addition, examples of optical plastics include, but are not limited to, acrylic, styrenic, polycarbonate, polyolefinic, and other optical plastics. The refractive index is preferably 1.3 to 1.9. The refractive index is more preferably 1.45 to 1.85.

In addition, there may be a space between the end face of the light guide and the lens, or the shape of the end face of the plastic optical fiber inserted in the light guide may be made identical to the shape of the lens for lighting so that there can be no space in between. When there is a space just corresponding to the minimum lens thickness, the space may be filled with air or may be filled with transparent liquid or solid or transparent resin.

It is preferable that the medical device lighting includes a light source and a light guide which transmits light from the light source to an end of the light guide and radiates the light to an irradiated object, wherein the plastic optical fiber side of the lens for lighting has a plane surface. Allowing this side of the lens to have a plane surface makes it possible to consider a desired glass thickness without taking into consideration the minimum lens thickness corresponding to the curvature radius, to make the cost lower and, furthermore, to more easily align the lens and the light guide concentrically.

The medical device lighting may include a light source and a light guide that transmits light from the light source to an end of the light guide and radiates the light to an irradiated object, but the medical device lighting may have no lens for lighting on the end of the light guide. That is, the medical device lighting can optionally be free of a lens for lighting.

Examples of medical devices for which such a medical device lighting as above-mentioned can be used include endoscopes, particularly preferably endoscopes an observation probe of which can be inserted into the bile duct or the pancreatic duct.

EXAMPLES

Below, our POFs and medical device lighting will be described in further detail with reference to Examples. In this regard, the produced POFs were evaluated by the following methods:

Fluorine content: determined by elemental analysis

Refractive index: measured using an Abbe's refractometer as measuring equipment under an atmosphere having a room temperature of 25° C.

Translucency: measured by a 30/2 m cutting-back method using a parallel light from a halogen lamp (at a wavelength of 650 nm)

Number of consecutive bendings before breaking: a load of 200 g was applied to one end of a cord, which was supported with a mandrel having a diameter of 30 mm; the other end of the fiber was consecutively bent at an angle of 90° with the supporting point in the center, and the number of bendings required to break the fiber was counted (the average was taken at n=5).

Curvature radius of lens for lighting: measured using a laser interferometer

Lens concave thickness of lens for lighting: as in FIG. 1, the minor axis width of the lens for lighting 2 was made identical to the minor axis width of the light guide 1, and the lens concave thickness 3 was determined.

Lens width of lens for lighting: as in FIG. 3, the lens concave thickness 3 was made half of the minor axis diameter, $FL_S$, of the light guide, and the lens width 4 was determined.

Example 1

A cladding material was fed into a conjugate spinner, wherein the cladding material was a vinylidene fluoride (2F)/tetrafluoroethylene (4F)/hexafluoropropylene (6F)/perfluoropropylvinyl ether copolymer (having a refractive index of 1.360 and a fluorine content of 71.7%) having the copolymerization ratio shown in Table 1. Furthermore, PMMA (having a refractive index of 1.492) produced by continuous bulk polymerization was fed as a core material into a conjugate spinner, and the core and the cladding were allowed to undergo core-cladding conjugate melt spinning at 235° C. to obtain a bare fiber having a fiber diameter of 500 µm (having a core diameter of 486 µm and a cladding thickness of 7.0 µm). To serve as a light guide of a medical device lighting, the optical fiber was further coated with polyethylene to be formed into a cord having an outer diameter of 1.0 mm. That is, the minor axis diameter of the end face of the light guide was 1.0 mm.

The thus obtained POF was evaluated by the above-mentioned evaluation methods related to translucency and the number of consecutive bendings before breaking. The results are shown in Table 1. Table 1 has revealed that this POF has a high numerical aperture and good translucency and repeated bending properties, and is suitable as a plastic optical fiber for a medical device lighting.

Next, the scattered light from the light guide was measured. The method was as follows: a 30 m cord coated with polyethylene was prepared; both end faces of the fiber were treated on a hot plate; and then, a lens for lighting (a spherical plane-concave lens, manufactured by SIGMA-KOKI Co., LTD., made of a material, BK7, and having a refractive index of 1.517) was attached to one of the end faces such that the concave surface side of the lens was in contact with the end of the cord, wherein the lens for lighting had a plano-concave shape to have a lens concave thickness of 0.13 mm and a lens width of 1.7 mm and satisfy $R_S/FL_S=1.0$. In a darkroom, light was radiated into the other end face using a 50 W halogen lamp light source (manufactured by USHIO LIGHTING, INC.), and the light outgoing from the lens for lighting was projected on sheets of paper disposed to correspond to the distances of the light. The diameter of the expanse of the light on each sheet of paper was measured. As a result, the radius of the expanse at the position 5.3 cm away from the lens for lighting was 9.9 cm.

Example 2

A cladding material was fed into a conjugate spinner, wherein the cladding material was a vinylidene fluoride (2F)/tetrafluoroethylene (4F) copolymer (having a refractive index of 1.405 and a fluorine content of 64%) having the copolymerization ratio shown in Table 1. Furthermore, PMMA (having a refractive index of 1.492) produced by continuous bulk polymerization was fed as a core material into a conjugate spinner, and the core and the cladding were allowed to undergo core-cladding conjugate melt spinning at 235° C. to obtain a bare fiber having a fiber diameter of 500 µm (having a core diameter of 486 µm and a cladding thickness of 7.0 µm). The optical fiber was further coated with polyethylene to be formed into a cord having an outer diameter of 1.0 mm.

The thus obtained POF was evaluated by the above-mentioned evaluation methods related to translucency and the number of consecutive bendings before breaking. The results are shown in Table 1. Table 1 has revealed that, compared to Example 1, this POF has a low numerical aperture but has good translucency and repeated bending properties, and is suitable as a plastic optical fiber for a medical device lighting.

Next, a lens for lighting was attached to an end of the cord such that the concave surface side of the lens was in contact with the end of the cord, wherein the lens for lighting had a plano-concave shape to have a lens concave thickness of 0.13 mm and a lens width of 1.7 mm and satisfy $R_S/FL_S=1.0$. Light was radiated into the opposite end face of the cord from the lens for lighting, and the radius of the expanse of the light at the position 5.3 cm away from the lens for lighting was found to be 7.2 cm.

Examples 3 to 10, Reference Examples 1 to 2, and Comparative Examples 1 to 2

A POF or a glass fiber was obtained in the same manner as in Example 1 except that the core material or the cladding material was changed as in Table 1. These fibers were used and evaluated in the same manner as in Example 1.

Further in Examples 3 to 7 and 9 to 10, Reference Examples 1 to 2, and Comparative Examples 1 to 2, a lens for lighting was attached to an end of each cord such that the concave surface side of the lens was in contact with the end of the cord, wherein the lens for lighting had a plano-concave shape so that the values of the lens concave thickness, the lens width, and $R_S/FL_S$ could be as shown in Table 1. In Example 8, no lens for lighting was used. In Example 9, a lens for lighting in plane shape was used. In Example 10, the design of the light guide was changed as shown in Table 1.

In each of Examples, Reference Examples, and Comparative Examples, the expanse of the light at the position 5.3 cm away from the lens for lighting was measured in the same manner as in Example 1. The evaluation results and the like are shown in Table 1.

Examples 3 to 10 presented both excellent translucency and repeated bending properties, and were each suitable as a plastic optical fiber for a medical device lighting.

Examples 3 and 4 in which a lens having a lens concave thickness of 0.13 mm was used showed the suitable result that the expanse of the light at the position 5.3 cm away from the lens for lighting was 10.2 cm and 10.4 cm respectively.

In Example 5, a lens for lighting was used for a cord produced using a fiber having the same composition as in Example 3, wherein the lens for lighting had a plano-concave shape to have a lens concave thickness of 0.27 mm and a lens width of 1.2 mm and satisfy $R_S/FL_S=0.6$, and the expanse of the light at the position 5.3 cm away from the lens for lighting was found to be wide, 11.9 cm, but because of this, the lens concave thickness had to be made thicker, 0.27 mm.

In Example 6, a lens for lighting was used for a cord produced using a fiber having the same composition as in Example 3, wherein the lens for lighting had a plano-concave shape to have a lens concave thickness of 0.06 mm and a lens width of 2.6 mm and satisfy $R_S/FL_S=2.0$, and the expanse of the light at the position 5.3 cm away from the lens for lighting was found to be suitable, 8.9 cm, although the lens thickness was small, 0.06 mm.

In Example 7, a lens for lighting was used for a cord produced using a fiber having the same composition as in Example 3, wherein the lens for lighting had a plano-concave shape to have a lens concave thickness of 0.18 mm and a lens width of 1.5 mm and satisfy $R_S/FL_S=0.8$, and the expanse of the light at the position 5.3 cm away from the lens for lighting was found to be wide, 11.1 cm, but because of this, the lens concave thickness had to be made a little thicker, 0.18 mm.

In Example 8, a lens for lighting was not attached to a cord produced using a fiber having the same composition as in Example 3, and evaluated as it was as a plastic optical fiber for a medical device lighting. The expanse of the light at the position 5.3 cm away from the end of the cord was suitable, 8.5 cm.

In Example 9, a lens for lighting in plane shape was used for a cord produced using a fiber having the same composition as in Example 3. The lens thickness did not need to be taken into consideration because the lens for lighting was plane. The expanse of the light at the position 5.3 cm away from the lens for lighting was suitable, 8.5 cm.

In Example 10, a fiber having the same composition as in Example 3 was used, but the cord was designed differently to have a fiber diameter of 0.25 mm and a cord diameter of 0.5 mm. A lens for lighting was used for the cord, wherein the lens for lighting had a plano-concave shape to have a lens concave thickness of 0.07 mm and a lens width of 0.9 mm and satisfy $R_S/FL_S=1.0$, and the expanse of the light at the position 5.3 cm away from the lens for lighting was found to be suitable, 10.0 cm.

In Comparative Example 1, the translucency and the repeated bending properties were both lower than in Examples. A lens for lighting was used at an end of the cord, wherein the lens for lighting had a plano-concave shape to satisfy $R_S/FL_S=1.0$, and the expanse of the light at the position 5.3 cm away from the lens for lighting was found to be 6.0 cm. This expanse of light was insufficient for an optical fiber for a medical device lighting.

In Comparative Example 2, a 1.0 mm cord including a bundle of glass fibers was used, wherein the bundle had a diameter of 0.5 mm and coated with polyethylene, and the cord had lower repeated bending properties than in Examples. A lens for lighting was used for the cord, wherein the lens for lighting had a plano-concave shape to satisfy $R_S/FL_S=1.0$, and the expanse of the light at the position 5.3 cm away from the lens for lighting was found to be 4.0 cm. This expanse of light was insufficient for an optical fiber for a medical device lighting.

TABLE 1

| | Core | First Cladding | | | Characteristic Evaluation Results | | |
| | | | | | | | |
| | Composition (Refractive Index) | Composition (wt %) | Refractive Index (Numerical Aperture) | Fluorine Content (wt %) | Translucency (dB/km) | Number of Consecutive Bendings | End Face of Light Guide $FL_S/FL_L$ |
|---|---|---|---|---|---|---|---|
| Example 1 | PMMA (1.492) | 2F/4F/6F/perfluoro-propylvinyl ether = 24/53/19/4 | 1.360 (0.61) | 71.7 | 131 | 43200 | 1.0 |
| Example 2 | PMMA (1.492) | 2F/4F/ = 74.5/25.5 | 1.405 (0.50) | 64 | 132 | 12000 | 1.0 |
| Example 3 | PMMA (1.492) | 2F/4F/6F/perfluoro-propylvinyl ether = 19/59/19/3 | 1.351 (0.63) | 72.8 | 128 | >50000 | 1.0 |
| Example 4 | PMMA (1.492) | 2F/4F/6F/perfluoro-propylvinyl ether = 16/66/16/2 | 1.348 (0.64) | 73.5 | 141 | 38200 | 1.0 |
| Example 5 | PMMA (1.492) | 2F/4F/6F/perfluoro-propylvinyl ether = 19/59/19/3 | 1.351 (0.63) | 72.8 | 128 | >50000 | 1.0 |
| Example 6 | PMMA (1.492) | 2F/4F/6F/perfluoro-propylvinyl ether = 19/59/19/3 | 1.351 (0.63) | 72.8 | 128 | >50000 | 1.0 |
| Example 7 | PMMA (1.492) | 2F/4F/6F/perfluoro-propylvinyl ether = 19/59/19/3 | 1.351 (0.63) | 72.8 | 128 | >50000 | 1.0 |
| Example 8 | PMMA (1.492) | 2F/4F/6F/perfluoro-propylvinyl ether = 19/59/19/3 | 1.351 (0.63) | 72.8 | 128 | >50000 | 1.0 |
| Example 9 | PMMA (1.492) | 2F/4F/6F/perfluoro-propylvinyl ether = 19/59/19/3 | 1.351 (0.63) | 72.8 | 128 | >50000 | 1.0 |
| Example 10 | PMMA (1.492) | 2F/4F/6F/perfluoro-propylvinyl ether = 24/53/19/4 | 1.360 (0.61) | 71.7 | 131 | 43200 | 1.0 |
| Reference Example 1 | PMMA (1.492) | 2F/4F/6F/trifluoro-ethylene = 19/59/19/3 | 1.358 (0.62) | 72.2 | 132 | 42300 | 1.0 |

TABLE 1-continued

|  | Curvature Radius of Minor Axis of Lens For Lighting $R_S$ (mm) | Minor Axis Diameter of End Face of Light Guide $FL_S$ (mm) | $R_S/FL_S$ | Lens Concave Thickness of Lens for Lighting (mm) | Lens Width of Lens for Lighting (mm) | Distance of Expanse of Light at Position 5.3 cm away from Radiating End Face (cm) |
|---|---|---|---|---|---|---|
| Example 1 | 1.0 | 1.0 | 1.0 | 0.13 | 1.7 | 9.9 |
| Example 2 | 1.0 | 1.0 | 1.0 | 0.13 | 1.7 | 7.2 |
| Example 3 | 1.0 | 1.0 | 1.0 | 0.13 | 1.7 | 10.2 |
| Example 4 | 1.0 | 1.0 | 1.0 | 0.13 | 1.7 | 10.4 |
| Example 5 | 0.6 | 1.0 | 0.6 | 0.27 | 1.2 | 11.9 |
| Example 6 | 2.0 | 1.0 | 2.0 | 0.06 | 2.6 | 8.9 |
| Example 7 | 0.8 | 1.0 | 0.8 | 0.18 | 1.5 | 11.1 |
| Example 8 | — | 1.0 | — | — | — | 8.5 |
| Example 9 | 1.0 | 1.0 | 1.0 | 0.35 | 1.7 | 8.5 |
| Example 10 | 0.5 | 0.5 | 1.0 | 0.07 | 0.9 | 10.0 |
| Reference Example 1 | 1.0 | 1.0 | 1.0 | 0.13 | 1.7 | 10.0 |

TABLE 1

|  | Core | First Cladding | | | | Characteristic Evaluation Results | | |
|---|---|---|---|---|---|---|---|---|
|  | Composition (Refractive Index) | Composition (wt %) | Refractive Index (Numerical Aperture) | Fluorine Content (wt %) | Translucency (dB/km) | Number of Consecutive Bendings | End Face of Light Guide $FL_S/FL_L$ |
| Reference Example 2 | PMMA (1.492) | 2F/4F/6F/hexa-fluoroacetone = 28/50/15/7 | 1.360 (0.61) | 70.6 | 130 | 23200 | 1.0 |
| Comparative Example 1 | PMMA (1.492) | MMA/4FM/5FM = 20/20/60 | 1.405 (0.46) | 34 | 136 | 3500 | 1.0 |
| Comparative Example 2 | Glass | Glass Fiber | 1.457 (0.22) | 0 | — | 200 | 1.0 |

|  | Curvature Radius of Minor Axis of Lens For Lighting $R_S$ (mm) | Minor Axis Diameter of End Face of Light Guide $FL_S$ (mm) | $R_S/FL_S$ | Lens Concave Thickness of Lens for Lighting (mm) | Lens Width of Lens for Lighting (mm) | Distance of Expanse of Light at Position 5.3 cm away from Radiating End Face (cm) |
|---|---|---|---|---|---|---|
| Reference Example 2 | 1.0 | 1.0 | 1.0 | 0.13 | 1.7 | 9.9 |
| Comparative Example 1 | 1.0 | 1.0 | 1.0 | 0.13 | 1.7 | 6.0 |
| Comparative Example 2 | 1.0 | 1.0 | 1.0 | 0.13 | 1.7 | 4.0 |

PMMA: polymethyl methacrylate
2F: vinylidene fluoride,
4F: tetrafluoroethylene,
6F: hexafluoropropylene

The invention claimed is:

1. A medical device lighting, comprising
1) a light source,
2) a light guide that transmits light from said light source to an end of said light guide and radiates said light to an irradiated object, wherein said light guide comprises a plastic optical fiber comprising a core and a cladding, said core is composed of a (co)polymer containing methyl methacrylate as a main component,
said cladding is composed of a copolymer having a fluorine weight composition ratio of 60 to 74%, and
said plastic optical fiber has a theoretical numerical aperture, NA, of 0.48 to 0.65, and
3) a lens for lighting disposed on said end face of said end, wherein the light guide side of said lens has a concave surface, and a curvature radius, Rs, of the minor axis of the lens and a minor axis diameter, FLs, of said end face of said light guide have a relationship of Rs/FLs>0.7.

2. The medical device lighting according to claim 1, wherein said cladding has a bending elastic modulus of 20 to 200 Mpa.

3. The medical device lighting according to claim 1, wherein said cladding is composed of a copolymer containing copolymerized components:

10 to 30 wt % of hexafluoropropylene,
45 to 75 wt % of tetrafluoroethylene,
10 to 35 wt % of vinylidene fluoride, and
1 to 10 wt % of perfluoroalkylvinylether;

said cladding is composed of a copolymer having a fluorine weight composition ratio of 70 to 74%; and said plastic optical fiber for a medical device lighting has a theoretical numerical aperture, NA, of 0.60 to 0.65.

4. The medical device lighting according to claim 1, wherein said cladding is composed of a copolymer containing copolymerized components:

14 to 25 wt % of hexafluoropropylene,
49 to 70 wt % of tetrafluoroethylene,
14 to 30 wt % of vinylidene fluoride, and
2 to 7 wt % of perfluoroalkylvinylether.

5. The medical device lighting according to claim 1, wherein said cladding has a thickness of 2 to 20 μm.

6. The medical device lighting according to claim 1, further comprising one or more cladding layers outside of said cladding, wherein the outermost cladding layer is composed of a copolymer containing 10 to 35 wt % of ethylene,
45 to 69 wt % of tetrafluoroethylene,
20 to 45 wt % of hexafluoropropylene, and
0.01 to 10 wt % of a fluorovinyl compound represented by Equation (1):

$$CH_2=CX^1(CF_2)_nX^2 \qquad (1)$$

wherein $X^1$ represents a fluorine atom or hydrogen atom; $X^2$ represents a fluorine atom, hydrogen atom, or carbon atom; and n is an integer of 1 to 10.

7. The medical device lighting according to claim 1, wherein the number of said plastic optical fibers is ten or less.

8. The medical device lighting according to claim 1, wherein the number of said plastic optical fiber is one.

9. The medical device lighting according to claim 1, wherein said plastic optical fiber has an outer diameter of 0.1 mm or more and 2.0 mm or less.

10. The medical device lighting according to claim 1, comprising an observation probe having an outer diameter of 7 mm or less.

11. The medical device lighting according to claim 1, further comprising a lens for lighting disposed on the end face of said end of said light guide, wherein a major axis diameter, $FL_L$, of said end face and a minor axis diameter, $FL_S$, of said end face have a relationship of $0.9 \le FL_S/FL_L \le 1$.

12. The medical device lighting according to claim 1, further comprising a lens for lighting disposed on said end, wherein the plastic optical fiber side of said lens for lighting has a plane surface.

13. The medical device lighting according to claim 1, wherein the medical device is an endoscope.

14. The medical device lighting according to claim 13, wherein an observation probe of said endoscope can be inserted into the bile duct or the pancreatic duct.

* * * * *

UNITED STATES PATENT AND TRADEMARK OFFICE
CERTIFICATE OF CORRECTION

PATENT NO. : 11,454,756 B2
APPLICATION NO. : 16/646724
DATED : September 27, 2022
INVENTOR(S) : Kojima et al.

Page 1 of 1

It is certified that error appears in the above-identified patent and that said Letters Patent is hereby corrected as shown below:

In the Specification

<u>At Column 1</u>
At Line 66, please change "Core)" to --Core)$^2$--.

Signed and Sealed this
Nineteenth Day of September, 2023

Katherine Kelly Vidal
*Director of the United States Patent and Trademark Office*